(12) United States Patent
Knopff

(10) Patent No.: US 7,332,633 B2
(45) Date of Patent: Feb. 19, 2008

(54) PROCESS FOR THE PREPARATION OF OPTICALLY ACTIVE CYCLOHEXENONES

(75) Inventor: Oliver Knopff, Geneva (CH)

(73) Assignee: Firmenich SA, Geneva (CH)

( * ) Notice: Subject to any disclaimer, the term of this patent is extended or adjusted under 35 U.S.C. 154(b) by 15 days.

(21) Appl. No.: 11/484,451

(22) Filed: Jul. 10, 2006

(65) Prior Publication Data

US 2006/0252967 A1 Nov. 9, 2006

Related U.S. Application Data

(63) Continuation of application No. PCT/IB2005/000399, filed on Feb. 15, 2005.

(30) Foreign Application Priority Data

Feb. 16, 2004 (EP) .................................. 04100615

(51) Int. Cl.
*C07C 45/67* (2006.01)

(52) U.S. Cl. ...................................... 568/341; 568/343
(58) Field of Classification Search ..................... None
See application file for complete search history.

(56) References Cited

FOREIGN PATENT DOCUMENTS

GB 1211 697 A 11/1970

OTHER PUBLICATIONS

C. Agami et al., XP-002285952, "Enantioselective cyclizations of acyclic 1,5-diketones" Bulletin De La Societe Chimique De France, No. 2, pp. 358-360 (1987).

*Primary Examiner*—Sikarl A. Witherspoon
(74) *Attorney, Agent, or Firm*—Winston & Strawn LLP

(57) ABSTRACT

The present invention relates to a process for the preparation of an optically active 5-substituted cyclohexenone (II) by treating an achiral macrocyclic 3-substituted-1,5-diketone (I) in the presence of an optically active sodium, potassium or cesium alkoxide.

13 Claims, No Drawings

PROCESS FOR THE PREPARATION OF OPTICALLY ACTIVE CYCLOHEXENONES

CROSS-REFERENCE TO RELATED APPLICATIONS

This application is a continuation of International application PCT/IB2005/000399 filed Feb. 15, 2005, the entire content of which is expressly incorporated herein by reference thereto.

TECHNICAL FIELD

The present invention relates to the field of organic synthesis and more specifically to a process for the preparation of an optically active 5-substituted cyclohexenone by treating an achiral macrocyclic 3-substituted-1,5-diketone in the presence of an optically active sodium, potassium or cesium alkoxide, according to Scheme 1:

Scheme 1: the process of the invention (I) → (II)

BACKGROUND

Optically active cyclohexenone derivatives are useful intermediates or building-blocks for the synthesis of various more complex compounds, such as steroids or macrocyclic ketones.

Despite this fact, to the best of our knowledge, the prior art reports only one process to carry out the cyclisation of an achiral di-ketone, in the presence of a chiral promoter, into an optically active cyclohexenone derivative (see C. Agami et al. in Bulletin de la Société Chimique de France, 1987, 358).

However said method is very specific in both the nature of the chiral promoter and in the substrate used, and therefore suffers from the drawback of being of very little versatility.

Indeed, there is disclosed only one possible chiral promoter of the cyclisation, i.e. the amino acid (S)-proline, and only a specific type of di-ketone, i.e. a 4-alkyl-2,6-heptanedione.

Moreover, the prior art does not provide any suggestion or information concerning the possibility to carry out said process with other promoters or with other substrates. Concerning the substrate, it is also useful to point out that said 4-alkyl-2,6-heptanediones are known to be more easily activated to perform aldol reactions than, for instance, a macrocyclic 1,5-di-ketone. In fact we have noticed that by applying the prior art experimental conditions to a macrocyclic 1,5-di-ketone the corresponding optically active cyclohexenone is not obtained.

Therefore, the prior art does not solve the problem of providing a process for the preparation of an optically active cyclohexenone starting from an achiral di-ketone and which is of a more broad scope in the nature of the starting material and/or in the nature of the chiral compound used to promote the aldol reaction, i.e. the cyclisation, allowing thus a greater versatility. Moreover, in particular, the prior art does not provide a solution to the problem of providing a process for the preparation of an optically active cyclohexenone derivative starting from an achiral macrocyclic di-ketone.

SUMMARY OF THE INVENTION

The present invention now relates about a process for the preparation of an optically active compound of formula (II) as defined below, starting from a substituted 1,5-dione, and using as promoter optically active sodium, potassium or cesium alkoxydes, preferably said alkoxydes are obtained from 1,2-aminoalcohols.

DETAILED DESCRIPTION OF THE PREFERRED EMBODIMENTS

In order to solve the problem above mentioned the present invention relates to a process, aimed at the synthesis of an optically active cyclohexenone derivative, in a single step, via an intramolecular aldol condensation.

Therefore the invention concerns a process for the preparation of a compound of formula (II)

wherein the $R^1$ represents a linear $C_7$-$C_9$ alkanediyl or alkenediyl group optionally substituted;

$R^2$ represents a $C_{1-6}$ linear, branched or cyclic alkyl or alkenyl group optionally substituted or a phenyl group optionally substituted; and the asterisk means that said compound (II) is in an optically active form;

by treating an achiral di-ketone, the substrate, of formula (I)

wherein $R^1$ and $R^2$ have the meaning indicated in formula (II), in the presence of an optically active sodium, potassium or cesium alkoxide.

As mentioned above, $R^1$ and $R^2$ can be substituted, for example by up to two groups. As non-limiting examples, said groups are R or OR groups or even halogen atoms, wherein R stands for methyl or ethyl. Said $R^1$ group may also comprise a $C_{3-4}$ acetal group.

According to a preferred embodiment of the invention, R represents a $C_{1-6}$ linear, branched or cyclic alkyl group.

More preferably, the compound of formula (I) is 3-methyl-1,5-cyclopentadecanedione, and therefore the compound of formula (II) is (S)-14-methyl-bicyclo[9.4.0]pentadec-1(11)-en-12-one or (R)-14-methyl-bicyclo[9.4.0]pentadec-1(11)-en-12-one or an optically active mixture of said stereoisomers.

As mentioned above, the invention's process is performed in the presence of an optically active sodium, potassium or cesium alkoxide.

By "optically active alkoxide" we mean here a compound comprising at least one moiety having an alkoxy group, i.e. a deprotonated alcohol group, and which is optically active. In other words, said optically active alkoxide can be an optically active sodium, potassium or cesium salt of a $C_4$-$C_{40}$ compound comprising one, two or three of such moieties or of a carbohydrate, such as a sugar, or of a polymer comprising optically active alkoxy groups.

Although it is not possible to provide an exhaustive list of the currently known optically active sodium, potassium or cesium alkoxides which can be used in the invention's process, the following can be named as preferred examples:

a) a sodium, potassium or cesium salt of a $C_4$-$C_{18}$ optically active mono alcohol, such as a sodium, potassium or cesium salt of an optically active alcohol of formula

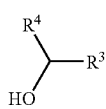

(III)

wherein $R^3$ represents a $C_{1-4}$ alkyl group or an optionally substituted phenyl group and $R^4$ represents a $C_{1-4}$ alkyl group or a $C(R^5)_2(OR^{4'})$ group, $R^5$ representing a hydrogen atom or a $R^3$ group and $R^{4'}$ representing a $C_{1-6}$ alkyl group, an optionally substituted phenyl or benzyl group or a $C_{3-9}$ trialkyl silyl or a triphenyl silyl group; or such as a chiral alcohol of formula $R^{3'}$—OH, wherein $R^{3'}$ represents a $C_{7-12}$ chiral hydrocarbon group;

b) a sodium, potassium or cesium salt of
a $C_3$-$C_{18}$ optically active 1,2-diol, such as a sodium, potassium or cesium salt of an optically active diol of formula

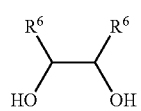

(IV)

wherein each $R^6$ represents an optionally substituted phenyl group, a $C_{1-6}$ alkyl group or a $COOR^7$ group, $R^7$ representing a $C_{1-4}$ alkyl group;

a $C_4$-$C_{18}$ optically active 1,3-diol, such as a sodium, potassium or cesium salt of an optically active diol of formula

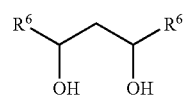

(V)

wherein each $R^6$ has the meaning indicated above;

a $C_5$-$C_{35}$ optically active 1,4-diol, such as a sodium, potassium or cesium salt of an optically active diol containing a moiety of formula

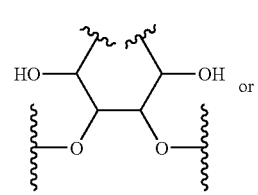

(VI)

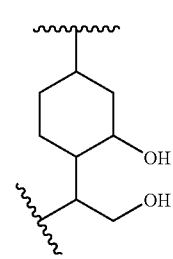

(VI')

or such as a sodium, potassium or cesium salt of an optically active diol of formula

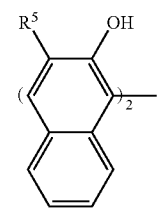

(VII)

wherein $R^5$ has the meaning indicated above;

c) a sodium, potassium or cesium salt of a $C_4$-$C_{25}$ optically active alcohol containing a nitrogen in the β position, such as a sodium, potassium or cesium salt of an optically active 1,2-amino-alcohol of formula

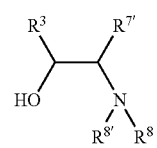

(VIII)

wherein $R^3$ has the meaning indicated above, $R^{7'}$ represents a $R^4$ or $R^5$ group as defined above and $R^8$ represents an optionally substituted phenyl group or a $C_{1-9}$ alkyl or alkylbenzene group and $R^{8'}$ represents a $R^8$ group or a $SO_2R^3$, $R^3CO$, $CH_2CH_2NR^3_2$, $SiR^3_3$, $PO(OR^3)_2$ group; optionally $R^3$ and $R^{7'}$ can be bonded together to form a $C_{5-10}$ ring or $R^{7'}$ and R⁸ can be bonded together to form a $C_{4-5}$ heterocycle, or R⁸ and R⁸' can be bonded together to form a $C_{2-5}$ heterocycle;

or such as a sodium, potassium or cesium salt of an optically active iminoalcohol of formula

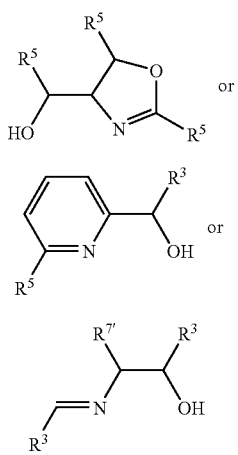

wherein each R³, R⁵ and R⁷' have the meaning indicated above;

d) a sodium, potassium or cesium salt of a $C_{15-38}$ compound having two or three groups derived from an optically active alkoxide mentioned under a), b) or c); or e) a sodium, potassium or cesium salt of an optically active alkoxide mentioned under d) and which is supported on an insoluble material such as silica, Merrifield resins, gold or polystyrenes.

Examples of substituents of phenyl groups are Cl, F, Br, R', SR', SO₂R', SOR', NO₂, NR'₂ or OR' groups, wherein R' stands for a $C_{1-4}$ alkyl group. Said aromatic rings can be substituted by one or two of said groups.

According to a particular embodiment of the invention, said optically active sodium, potassium or cesium alkoxide comprises one or two alkoxy groups and is:

a) a sodium, potassium or cesium salt of an optically active alcohol of formula

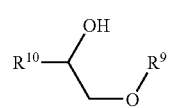

wherein R⁹ represents a $C_{1-4}$ alkyl group or an optionally substituted phenyl or benzyl group and R¹⁰ represents a phenyl group optionally substituted by one $C_{1-4}$ alkyl group;

b) a sodium, potassium or cesium salt of an optically active 1,2-diol of formula

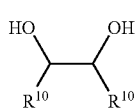

wherein each R¹⁰ has the meaning indicated above;

or a sodium, potassium or cesium salt of an optically active 1,4-diol of formula

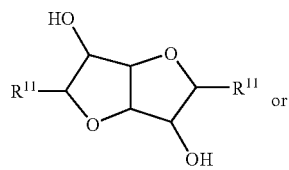

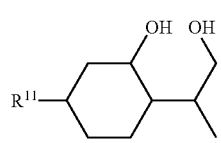

wherein each R¹¹ represents a $C_{1-4}$ group or an hydrogen atom;

c) a sodium, potassium or cesium salt of an optically active 1,2-amino alcohol of formula

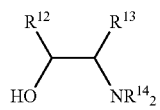

wherein R¹² represents a phenyl group optionally substituted by a Cl, Br, SO₂Me, F, SMe, OMe, NO₂ or $C_{1-4}$ alkyl group, R¹³ represents a $C_{1-4}$ alkyl group, a R¹² group or a $CH_2OSi(R^{13})_3$ group and R¹⁴ represents a benzyl or $C_{1-4}$ alkyl, or the two R¹⁴ are bonded together to form a $C_{4-5}$ heterocycle;

or a sodium, potassium or cesium salt of an optically active 1,2-imino alcohol of formula

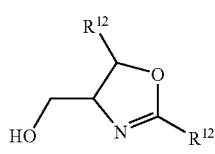

wherein each R¹² has the meaning indicated above; or d) a sodium, potassium or cesium salt of an optically active alcohol of formula

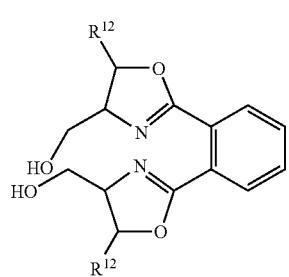

wherein each R¹² has the meaning indicated above.

Specific examples of the above mentioned optically active sodium, potassium or cesium alkoxides are a sodium, potassium or cesium salt of any one of the compounds of formula 1 to 12:

a)

(1)
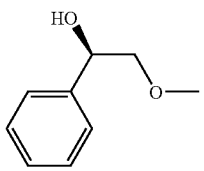

b)

(2)
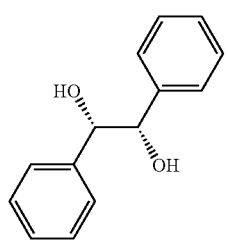

(3)
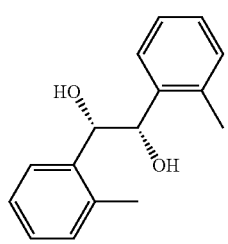

(4)
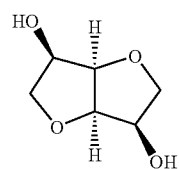

c)

(5)
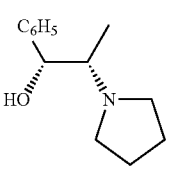

(6)
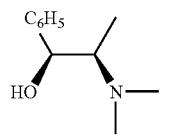

(7)

-continued (8)
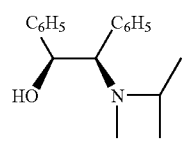

(9)
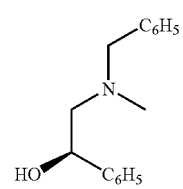

(10)
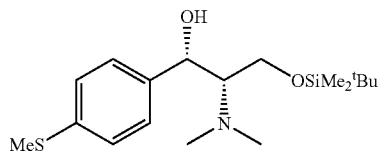

(11)
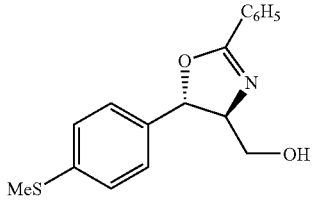

d)

(12)
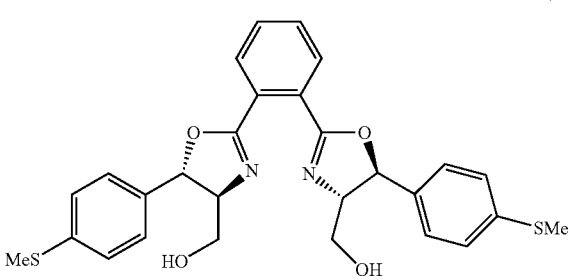

the dotted line representing a single or double bond;

said compounds having proved to be particularly useful for the invention's process wherein the starting compound (I) is a macrocycle.

It is also useful to mention that the optically active alkoxide can be characterized by a specific enantiomeric excess (e.e.). In general, optically active alkoxide having a higher e.e. provided compounds (I) with higher e.e. Therefore, it is preferable to employ in the invention's process optically active alkoxide having e.e. of at least 50% or even of at least 90%.

The optically active alkoxide can be added to the reaction medium in a large range of concentration. As non-limiting examples, one can cite as optically active alkoxide concentration values ranging from 0.2 to 20 molar equivalents, relative to the di-ketone (I). Preferably, the optically active alkoxide concentration will be comprised between 1.0 and 8.0 molar equivalents. It goes without saying that the optimum concentration of said alkoxide will depend on the nature of the latter and on the desired time of reaction.

The chiral sodium, potassium or cesium alkoxide can be in the form of a preformed salt or it can be formed in situ prior to its use, e.g. by pre-mixing a chiral compound comprising at least one moiety having a hydroxy group and an appropriate sodium, potassium or cesium base.

According to a particular embodiment of the invention the preferred alkoxides are the sodium or potassium alkoxides.

Furthermore, the process can be performed in the presence of an additive. Said additive is a compound capable of reacting with or trap water and is believed to favor the formation of the desired product.

Examples of useful additives are:
i) an alkaline or alkaline earth hydride, such as NaH, KH, CaH$_2$, LiH;
ii) a reaction-medium insoluble inorganic material capable to form a chlatrate with water, such as an anhydrous zeolite, preferably of the 4 Å type, or anhydrous NaOH, NaCl, Na$_2$CO$_3$, MgSO$_4$, Na$_2$SO$_4$, Na$_2$O, CaCl$_2$ or MgCl$_2$; or
iii) an organic material capable of reacting with water to form non-acidic compounds, such as an $^t$BuONa, orthoester, N-methyl-N-trimethylsilyl-trifluoroacetamide or 1-trimethylsilylimidazole.

According to a further embodiment of the invention, preferred additives are NaH, KH, anhydrous zeolite of the 4 Å type, $^t$BuONa or anhydrous KOH, NaOH, NaCl, Na$_2$CO$_3$, Na$_2$SO$_4$.

The additive can be added to the reaction medium in a large range of amounts which depend on the exact nature of the additive. However, the addition of amounts which exceed three times the amount theoretically needed to trap all the water which can theoretically be formed does not provide any appreciable additional benefit.

The process of the invention can be carried out in the presence or in the absence of solvent, but in any case it is advantageously performed under anhydrous conditions, e.g. in the presence of less than 0.5% w/w of water. As a person skilled in the art can anticipate, the presence of a solvent is mandatory only in the case in which the starting di-ketone (I) is a solid compound under the reaction conditions.

However, according to a preferred embodiment of the invention, and independently of the physical state of the starting di-ketone (I), the process is advantageously carried out in the presence of a solvent. Said solvent must be chemically compatible with the reaction and does not deactivate the alkoxide.

A suitable solvent is one which is aprotic. Non-limiting examples of such a solvent are ethers, esters, amides, amines, aromatic solvents, linear or branched or cyclic hydrocarbons, chlorinated solvents and mixtures thereof. More preferably, the solvent is a C$_4$-C$_6$ ether such as THF or dioxane, a C$_3$-C$_6$ amine such as NEt$_3$, pyridine, N-Me-pyrrolidine or N-Me-morpholine, C$_3$-C$_6$ amides such as DMF or N-Methyl pyrrolidone, methylene chloride, a C$_6$-C$_{10}$ aromatic solvent such as toluene or anisole, or mixtures thereof.

The temperature at which the process of the invention can be carried out is comprised between −20° C. and 100° C., preferably between 0° C. and 60° C. Of course a person skilled in the art is also able to select the preferred temperature as a function of the melting and boiling point of the starting and final products and/or an eventual solvent.

EXAMPLES

The invention will now be described in further detail by way of the following example, wherein the abbreviations have the usual meaning in the art, the temperatures are indicated in degrees centigrade (° C.); the NMR spectral data were recorded in CDCl$_3$ with a 360 MHz or 100 MHz machine for $^1$H or $^{13}$C respectively, the chemical displacements δ are indicated in ppm with respect to TMS as standard, the coupling constants J are expressed in Hz.

Example 1

Preparation of Optically Active 14-methyl-bicyclo[9.4.0]pentadec-1(11)-en-12-one

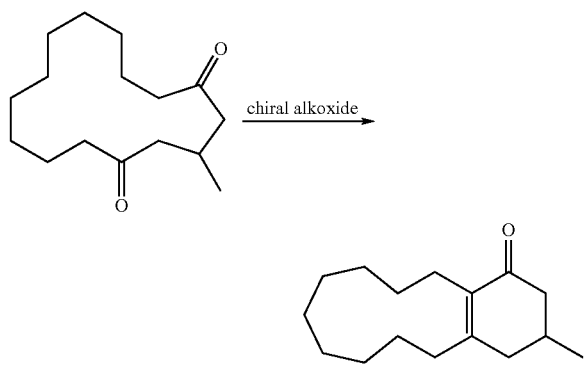

a) General Procedure:

In the reaction vessel, under inert atmosphere, were introduced 126 mg of 3-methyl-1,5-cyclopentadecanedione, 3 ml of dry THF, optionally 200 mg of anhydrous molecular sieve 4 Å or 2 molar equivalents of NaH, and the Na-alkoxide or K-alkoxide 1-12, according to Table 1, dissolved into dry THF. The total amount of THF present was calculated in order to keep the concentration of the starting dione between 0.1 and 0.4 mol/L at the beginning of the reaction.

The reaction mixture was stirred at room temperature and followed by GC. To stop the reaction the mixture was hydrolyzed with water or an aqueous 2N HCl solution. After extraction of the aqueous layer with diethyl ether the organic layer was dried over MgSO$_4$ and filtered. The solvent was removed under vacuum and the residue was purified either by flash chromatography or by bulb to bulb distillation to yield in the desired product, i.e. (S)-14-methyl-bicyclo [9.4.0]pentadec-1(11)-en12one or (R)-14-methyl-bicyclo [9.4.0]pentadec-1(11)-en-12-one or an optically active mixture of said stereoisomers depending on the configuration of the alkoxide.

$^1$H-NMR: 1.04(d, J=6.1 Hz, 3H), 1.18-1.46(m, 10H), 1.50-1.75(m, 4H), 1.97-2.15(m, 3H), 2.30-2.40(m, 3H), 2.41-2.56(m, 3H).

$^{13}$C-NMR: 21.3, 23.5, 24.6, 25.1, 25.3, 25.5, 26.0, 26.2, 26.6, 29.7, 32.3, 38.3, 46.7, 136.3, 158.2, 199.7.

The results obtained are shown in Table 1.

TABLE 1 yields and e.e. of the final product as a function of the alkoxide used.

| Alkoxide[1] | M[2] | Eq.[3] | t[4] | additive | Yield[5] | e.e[6] |
|---|---|---|---|---|---|---|
| 1 | Na | 2 | 14 | NaH | 99% | 44% ee (R) |
| 2 | Na | 2 | 3 | NaH | 93% | 31% ee (R) |
| 3 | Na | 2 | 2 | NaH | 80% | 31% ee (R) |
| 4 | Na | 1 | 6 | NaH | 35% | 18% ee (S) |
| 5 | Na | 1 | 6 | NaH | 23% | 26% ee (S) |
| 6 | Na | 4 | 3 | MS* | 76% | 39% ee (R) |
| 7 | Na | 8 | 3 | — | 99% | 74% ee (S) |

TABLE 1-continued yields and e.e. of the final product as a function of the alkoxide used.

| Alkoxide[1] | M[2] | Eq.[3] | t[4] | additive | Yield[5] | e.e[6] |
|---|---|---|---|---|---|---|
| 7 | K | 4 | 1 | MS* | 99% | 34% ee (S) |
| 7 | Cs | 4 | 46 | MS* | 75% | 42% ee (S) |
| 8 | Na | 4 | 3 | MS* | 69% | 59% ee (S) |
| 8 | K | 4 | 1.5 | MS* | 99% | 61% ee (S) |
| 9 | Na | 4 | 14 | NaH | 25% | 25% ee (S) |
| 10 | Na | 4 | 4 | NaH | 80% | 37% ee (S) |
| 11 | Na | 2 | 1 | NaH | 85% | 28% ee (R) |
| 12 | Na | 2 | 4 | NaH | 94% | 37% ee (R) |

*MS is molecular sieve
[1] see description
[2] metal of the alkoxide salt
[3] number of molar equivalent of alkoxide introduced, relative to the starting dione
[4] duration of the reaction in day
[5] determined by GC
[6] determined by reacting the final product with an excess of $LiAlH_4$ in dry THF. After hydrolysis, filtration and extraction in $Et_2O$, the allyl alcohol obtained was analyzed by GC with a chiral column (CHIRASIL DEX CB) to determine the enantiomeric excess of the resulting allyl alcohol.

What is claimed is:

1. A process for the preparation of a compound of formula

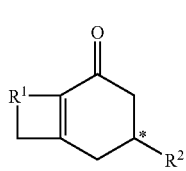

(II)

wherein the $R^1$ represents a linear $C_7$-$C_9$ alkanediyl or alkenediyl group that is optionally substituted;
$R^2$ represents a $C_{1-6}$ linear, branched or cyclic alkyl or alkenyl group that is optionally substituted or a phenyl group that is optionally substituted; and
the asterisk means that said compound (II) is in an optically active form;
by treating an achiral di-ketone, the substrate, of formula

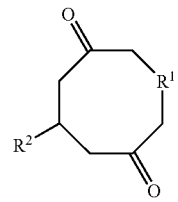

(I)

wherein $R^1$ and $R^2$ have the meaning indicated in formula (II),
in the presence of an optically active sodium, potassium or cesium alkoxide.

2. A process according to claim 1, wherein $R^2$ represents a $C_{1-6}$ linear, branched or cyclic alkyl group.

3. A process according to claim 1, wherein the compound of formula (I) is 3-methyl-1,5-cyclopentadecanedione, and the compound of formula (II) is (S)-14-methyl-bicyclo[9.4.0]pentadec-1(11)-en-12-one or (R)-14-methyl-bicyclo[9.4.0]pentadec-1(11)-en-12-one or an optically active mixture of said stereoisomers.

4. A process according to claim 1, wherein the optically active sodium, potassium or cesium alkoxide is an optically active sodium, potassium or cesium salt of a $C_4$-$C_{40}$ compound comprising one, two or three of alkoxy groups or of a carbohydrate or of a polymer comprising optically active alkoxy groups.

5. A process according to claim 1, wherein the optically active sodium, potassium or cesium alkoxide is:
a) a sodium, potassium or cesium salt of a $C_4$-$C_{18}$ optically active mono alcohol;
b) a sodium, potassium or cesium salt of a $C_3$-$C_{18}$ optically active 1,2-diol, a $C_4$-$C_{18}$ optically active 1,3-diol, a $C_5$-$C_{35}$ optically active 1,4-diol;
c) a sodium, potassium or cesium salt of a $C_4$-$C_{25}$ optically active alcohol containing a nitrogen in the β position;
d) a sodium, potassium or cesium salt of a $C_{15-38}$ compound having two or three groups derived from an optically active alkoxide mentioned under a), b) or c); or
e) a sodium, potassium or cesium salt of an optically active alkoxide, mentioned under d) and which is supported on an insoluble material.

6. A process according to claim 1, wherein the optically active sodium, potassium or cesium alkoxide is:
a) a sodium, potassium or cesium salt of an optically active alcohol of formula

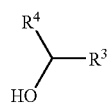

(III)

wherein $R^3$ represents a $C_{1-4}$ alkyl group or an optionally substituted phenyl group and $R^4$ represents a $C_{1-4}$ alkyl group or a $C(R^5)_2(OR^{4'})$ group, $R^5$ representing a hydrogen atom or a $R^3$ group and $R^{4'}$ representing a $C_{1-6}$ alkyl group, an optionally substituted phenyl or benzyl group or a $C_{3-9}$ trialkyl silyl or a triphenyl silyl group; or a chiral alcohol of formula $R^{3'}$—OH, wherein $R^{3'}$ represents a $C_{7-12}$ chiral hydrocarbon group;
b) a sodium, potassium or cesium salt of an optically active diol of formula

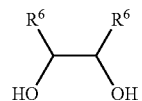

(IV)

wherein $R^6$ represents an optionally substituted phenyl group, a $C_{1-6}$ alkyl group or a $COOR^7$ group, $R^7$ representing a $C_{1-4}$ alkyl group;
a sodium, potassium or cesium salt of an optically active diol of formula

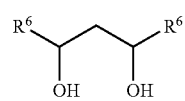

(V)

wherein each $R^6$ has the meaning indicated above;

a sodium, potassium or cesium salt of an optically active diol containing a moiety of formula

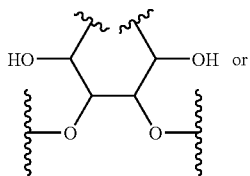

(VI)

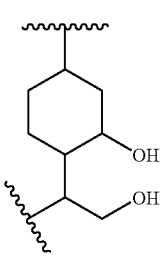

(VI')

a sodium, potassium or cesium salt of an optically active diol of formula

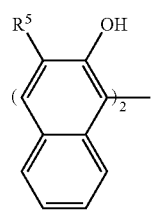

(VII)

wherein $R^5$ has the meaning indicated above;

c) a sodium, potassium or cesium salt of an optically active 1,2-amino-alcohol of formula

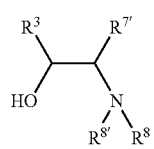

(VIII)

wherein $R^3$ has the meaning indicated above, $R^{7'}$ represents a $R^4$ or $R^5$ group as defined above and $R^8$ represents an optionally substituted phenyl group or a $C_{1-9}$ alkyl or alkylbenzene group and $R^{8'}$ represents a $R^8$ group or a $SO_2R^3$, $R^3CO$, $CH_2CH_2NR^3{}_2$, $SiR^3{}_3$, $PO(OR^3)_2$ group; optionally $R^3$ and $R^{7'}$ can be bonded together to form a $C_{5\text{-}10}$ ring or $R^{7'}$ and $R^8$ can be bonded together to form a $C_{4\text{-}5}$ heterocycle, or $R^8$ and $R^{8'}$ can be bonded together to form a $C_{2\text{-}5}$ heterocycle;

or a sodium, potassium or cesium salt of an optically active iminoalcohol of formula

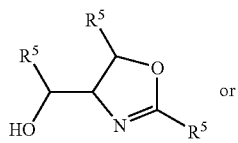

(IX)

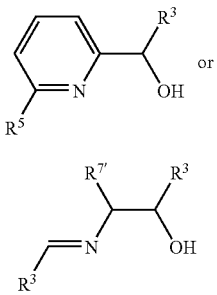

(IX')

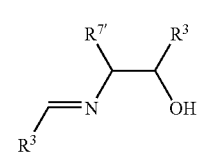

(IX'')

wherein each $R^3$, $R^5$ and $R^{7'}$ have the meaning indicated above;

d) a sodium, potassium or cesium salt of an optically active $C_{15\text{-}38}$ compound having two or three groups derived from an optically active alkoxide mentioned under a), b) or c); or e) a sodium, potassium or cesium salt of an optically active compound mentioned under d) and which is supported on silica, a Merrifield resin, gold or a polystyrene.

7. A process according to claim 1, wherein the optically active sodium, potassium or cesium alkoxide is:

a) a sodium, potassium or cesium salt of an optically active alcohol of formula

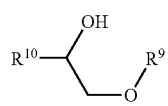

(X)

wherein $R^9$ represents a $C_{1-4}$ alkyl group or an optionally substituted phenyl or benzyl group and $R^{10}$ represents a phenyl group optionally substituted by one $C_{1-4}$ alkyl group;

b) a sodium, potassium or cesium salt of an optically active 1,2-diol of formula

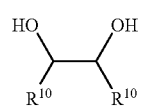

(XI)

wherein each $R^{10}$ has the meaning indicated above;

or a sodium, potassium or cesium salt of an optically active 1,4-diol of formula

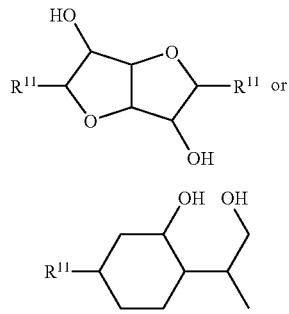
(XII)

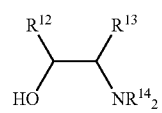
(XII')

wherein each $R^{11}$ represents a $C_{1-4}$ group or a hydrogen atom;

c) a sodium, potassium or cesium salt of an optically active 1,2-amino alcohol of formula

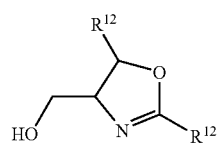
(XIII)

wherein $R^{12}$ represents a phenyl group optionally substituted by a Cl, Br, $SO_2Me$, F, SMe, OMe, $NO_2$ or $C_{1-4}$ alkyl group, $R^{13}$ represents a $C_{1-4}$ alkyl group, a $R^{12}$ group or a $CH_2OSi(R^{13})_3$ group and $R^{14}$ represents a benzyl or $C_{1-4}$ alkyl, or the two $R^{14}$ are bonded together to form a $C_{4-5}$ heterocycle;

or a sodium, potassium or cesium salt of an optically active 1,2-imino alcohol of formula (XIV)

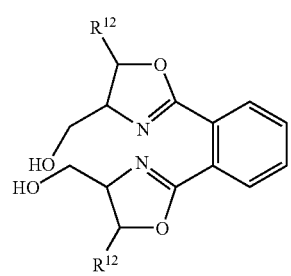

wherein each $R^{12}$ has the meaning indicated above; or d) a sodium, potassium or cesium salt of an optically active alcohol of formula (XV)

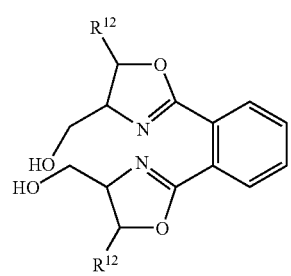

wherein each $R^{12}$ has the meaning indicated above.

8. A process according to claim 1, wherein the optically active sodium, potassium or cesium alkoxide is a sodium, potassium or cesium salt of any one of the compounds of formula 1 to 12:

a)

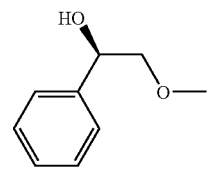
(1)

b)

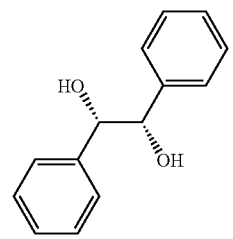
(2)

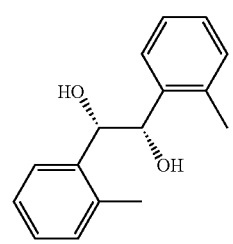
(3)

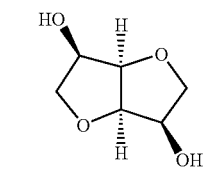
(4)

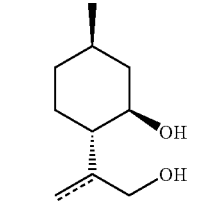
(5)

c)

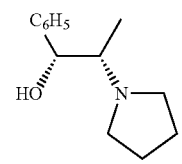
(6)

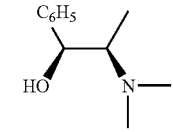
(7)

-continued

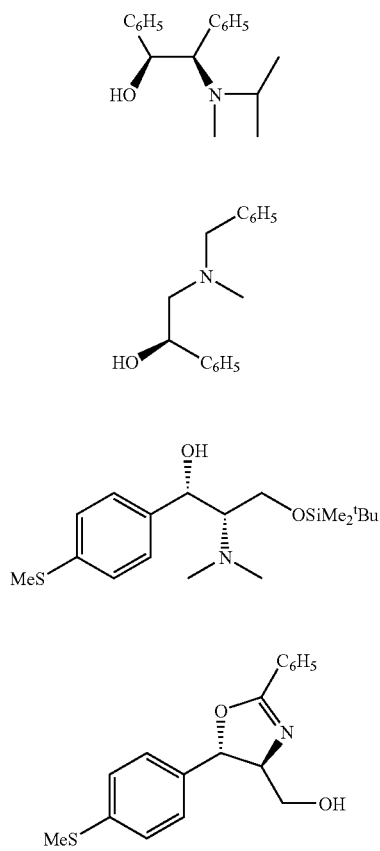

d)

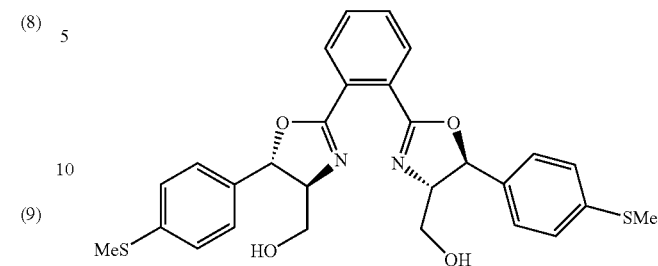

the dotted line representing a single or double bond.

9. A process according to claim 1, wherein the optically active alkoxide has an e.e. of at least 90%.

10. A process according to claim 1, wherein the optically active alkoxide is a sodium or potassium optically active alkoxide.

11. A process according to claim 1, wherein said process is carried out in the presence of an additive selected from the group consisting of
   i) an alkaline or alkaline earth hydride;
   ii) a reaction-medium insoluble inorganic material capable to form a chlatrate with water; and
   iii) an organic material capable of reacting with water to form non-acidic compounds.

12. A process according to claim 11, wherein the additive is selected from the group consisting of NaH, KH, anhydrous zeolite of the 4 Å type, $^t$BuONa or anhydrous KOH, NaOH, NaCl, $Na_2CO_3$, $Na_2SO_4$.

13. A process according to claim 1, wherein the process is carried out in the presence of a solvent and said solvent is selected from the group consisting of a $C_4$-$C_6$ ether, a $C_3$-$C_6$ amine, a $C_3$-$C_6$ amides, methylene chloride, a $C_6$-$C_{10}$ aromatic solvent and mixtures thereof.

* * * * *